US00PP20197P2

(12) United States Plant Patent
Bergman

(10) Patent No.: US PP20,197 P2
(45) Date of Patent: Aug. 4, 2009

(54) ***CHRYSANTHEMUM* PLANT NAMED 'CURRANT YOMISTIQUE'**

(50) Latin Name: *Chrysanthemum×morifolium*
Varietal Denomination: Currant Yomistique

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/214,226

(22) Filed: Jun. 16, 2008

(51) Int. Cl.
*A01H 5/00* (2006.01)

(52) U.S. Cl. ..... Plt./296

(58) Field of Classification Search ..... Plt./296
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Currant Yomistique', characterized by its compact, upright and uniformly mounded plant habit; freely branching and vigorous growth habit; small dark green-colored foliage; uniform, early and freely flowering habit; daisy-type inflorescences with deep coral bronze-colored ray florets; and excellent postproduction longevity.

1 Drawing Sheet

Botanical designation: *Chrysanthemum×morifolium.*
Cultivar denomination: 'Currant Yomistique'.

BACKGROUND OF THE INVENTION

The present invention relates to a new and distinct cultivar of *Chrysanthemum* plant, botanically known as *Chrysanthemum×morifolium,* commercially grown as a pot-type *Chrysanthemum* and hereinafter referred to by the name 'Currant Yomistique'.

The new *Chrysanthemum* is a naturally-occurring whole plant mutation of the *Chrysanthemum×morifolium* cultivar 'Yomistique', disclosed in U.S. Plant Pat. No. 17,412. The new *Chrysanthemum* was discovered and selected by the Inventor in a controlled greenhouse environment as a single flowering plant within a population of plants of 'Yomistique' in December, 2004, in Fort Myers, Fla.

Asexual reproduction of the new *Chrysanthemum* by vegetative tip cuttings was first conducted in a controlled greenhouse environment in Fort Myers, Fla. in March, 2005. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Currant Yomistique'. These characteristics in combination distinguish 'Currant Yomistique' as a new and distinct pot-type *Chrysanthemum* cultivar:

1. Compact, upright and uniformly mounded plant habit.
2. Freely branching and vigorous growth habit.

3. Small dark green-colored foliage.
4. Uniform, freely and early flowering habit.
5. Daisy-type inflorescences with deep coral bronze-colored ray florets.
6. Excellent postproduction longevity with inflorescences maintaining good substance and color for about five weeks in an interior environment.

Plants of the new *Chrysanthemum* differ from plants of the parent, 'Yomistique', in the following characteristics:

1. Plants of the new *Chrysanthemum* flower more uniformly than plants of 'Yomistique'.
2. Plants of the new *Chrysanthemum* and 'Yomistique' differ in ray floret color as plants of 'Yomistique' have purple-colored ray florets.

Plants of the new *Chrysanthemum* differ from plants of *Chrysanthemum×morifolium* 'Frosty Yomistique', U.S. Plant Patent application filed concurrently, primarily in ray floret color as plants of 'Frosty Yomistique' have white-colored ray florets.

Plants of the new *Chrysanthemum* can be compared to plants of *Chrysanthemum×morifolium* 'Dark Bronze Cherie', disclosed in U.S. Plant Pat. No. 18,362. In side-by-side comparisons conducted in Fort Myers, Fla., plants of the new *Chrysanthemum* differed from plants of 'Dark Bronze Cherie' in the following characteristics:

1. Plants of the new *Chrysanthemum* flowered two weeks earlier than plants of 'Dark Bronze Cherie'.
2. Inflorescences of plants of the new *Chrysanthemum* and 'Dark Bronze Cherie' differed in ray floret color as plants of 'Dark Bronze Cherie' had dark bronze-colored ray florets.

BRIEF DESCRIPTION OF THE PHOTOGRAPH

The accompanying photograph illustrates the overall appearance of the new *Chrysanthemum.* This photograph shows the colors as true as it is reasonably possible to obtain in colored reproductions of this type. Colors in the photograph may differ slightly from the color values cited in the detailed botanical description which accurately describe the colors of the new *Chrysanthemum*. The photograph comprises a side perspective view of typical flowering plants of 'Currant Yomistique' grown in a container.

DETAILED BOTANICAL DESCRIPTION

The aforementioned photograph and following observations and measurements describe plants grown in Leamington, Ontario, Canada during the autumn in a glass-covered greenhouse and under conditions and practices which approximate those generally used in commercial pot-type *Chrysanthemum* production. During the production of the plants, day temperatures ranged from about 21° C. to 27° C., night temperatures ranged from about 17° C. to 19° C. and light levels ranged from 4,000 to 6,000 foot candles. Four unrooted cuttings were directly stuck in 15-containers, exposed to long day/short night conditions, and pinched about three weeks later. At the time of the pinch, the photoinductive short day/long night treatments were started. Plants used in the photograph and for the description were grown as natural sprays and were eleven weeks from planting. In the following description, color references are made to The Royal Horticultural Society Colour Chart, 1995 Edition, except where general terms of ordinary dictionary significance are used.

Botanical classification: *Chrysanthemum ×morifolium* 'Currant Yomistique'.

Parentage: Naturally-occurring whole plant mutation of *Chrysanthemum×morifolium* 'Yomistique', disclosed in U.S. Plant Pat. No. 17,412.

Propagation:

*Type.*—Terminal vegetative cuttings.

*Time to initiate roots.*—About four days at temperatures of 21° C.

*Time to produce a rooted young plant.*—About ten days at temperatures of 21° C.

*Root description.*—Fine to thick, fibrous; white in color.

*Rooting habit.*—Freely branching; moderately dense.

Plant description:

*Appearance.*—Herbaceous daisy pot-type *Chrysanthemum* typically grown as a natural spray type. Compact; stems upright and outwardly spreading giving a uniformly mounded appearance to the plant. Freely branching habit, about four lateral branches develop after removal of terminal apex (pinching); dense and full plant habit. Moderately vigorous growth habit.

*Plant height.*—About 15 cm.

*Plant width.*—About 21 cm.

*Lateral branches.*—Length: About 11 cm. Diameter: About 3 mm. Internode length: About 1.4 cm. Strength: Strong. Texture: Pubescent. Color: Close to 144A.

Foliage description:

*Arrangement.*—Alternate, simple.

*Length.*—About 6.25 cm.

*Width.*—About 3.75 cm.

*Shape.*—Palmately lobed.

*Apex.*—Cuspidate.

*Base.*—Truncate.

*Margin.*—Palmately lobed, sinuses between lateral lobes divergent.

*Texture, upper and lower surfaces.*—Fine pubescence; veins prominent on lower surface.

*Color.*—Developing leaves, upper surface: More green than 147A. Developing leaves, lower surface: Close to 147B. Fully expanded leaves, upper surface: Close to 147A; venation, close to 147B. Fully expanded leaves, lower surface: Close to 147B; venation, close to 147B.

*Petiole.*—Length: About 1.5 cm. Diameter: About 3 mm. Texture, upper and lower surfaces: Pubescent. Color, upper surface: Close to 147B; towards the margin, close to 147A. Color, lower surface: Close to 147B.

Inflorescence description:

*Appearance.*—Daisy-type inflorescence form with elongated oblong-shaped ray florets. Inflorescences borne on terminals above foliage. Disc and ray florets arranged acropetally on a capitulum. Inflorescence slightly fragrant; pungent. Typically grown as a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about six weeks later.

*Postproduction longevity.*—Inflorescences maintain good color and substance for about five weeks in an interior environment. Quantity of inflorescences: Freely flowering, about five inflorescences develop per lateral stem.

*Inflorescence bud.*—Height: About 4 mm. Diameter: About 5 mm. Shape: Oblate. Color: Close to 141A.

*Inflorescence size.*—Diameter: About 2.9 cm. Depth (height): About 9 mm. Diameter of disc: About 1.4 cm. Receptacle height: About 5 mm. Receptacle diameter: About 5 mm. Receptacle color: Close to 144B.

*Ray florets.*—Shape: Elongated oblong. Orientation: Initially upright, then with development, close to perpendicular from vertical. Aspect: Initially incurved, then mostly flat. Length: About 1.3 cm. Width: About 4 mm. Apex: Emarginate, rounded or acute. Base: Attenuate; short corolla tube. Margin: Entire. Texture, upper and lower surfaces: Smooth, glabrous; satiny. Number of ray florets per inflorescence: About 20 arranged in a single whorl. Color: When opening and fully opened, upper surface: Close to 9A overlain with close to 53A; at the base, close to 9A. With development, close to 9A more faintly overlain with close to 53A. When opening and fully opened, lower surface: Close to 6A underlain with close to 53A to 53B.

*Disc florets.*—Arrangement: Massed at center of receptacle. Shape: Tubular, elongated. Apex: Five-pointed. Length: About 4 mm. Width, apex: About 1 mm. Width, base: About 1 mm. Number of disc florets per inflorescence: About 111. Color, immature: Apex: Close to 144A. Mid-section and base: Close to 155D. Color, mature: Apex: Close to 9A. Mid-section: Close to 154D. Base: Close to 155D.

*Phyllaries.*—Number of phyllaries per inflorescence: About 20 arranged in two or three whorls. Length: About 5 mm. Width: About 2.5 mm. Shape: Lanceolate. Apex: Acute. Base: Truncate. Margin: Entire. Texture, upper surface: Smooth, waxy. Texture, lower surface: Pubescent. Color, upper surface: Close to 141A. Color, lower surface: More green than 141A.

*Peduncles.*—Length: First peduncle: About 3.3 cm. Fourth peduncle: About 5 cm. Diameter (first peduncle): About 2 mm. Angle: About 30° from vertical. Strength: Strong, flexible. Texture: Pubescent. Color: Close to 144A.

*Reproductive organs.*—Androecium: Present on disc florets only. Stamen length: About 4 mm. Filament length: About 3 mm. Filament color: Close to 154D. Anther shape: Narrowly oblong. Anther length: Less than 1 mm. Anther color: Close to 9A. Pollen amount: None observed. Gynoecium: Present on both ray and disc florets. Pistil length: About 6 mm. Stigma shape: Bi-parted. Stigma color: Close to 9A. Style length: About 5 mm. Style color: Close to 154D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 38° C.

It is claimed:

1. A new and distinct *Chrysanthemum* plant named 'Currant Yomistique' as illustrated and described.

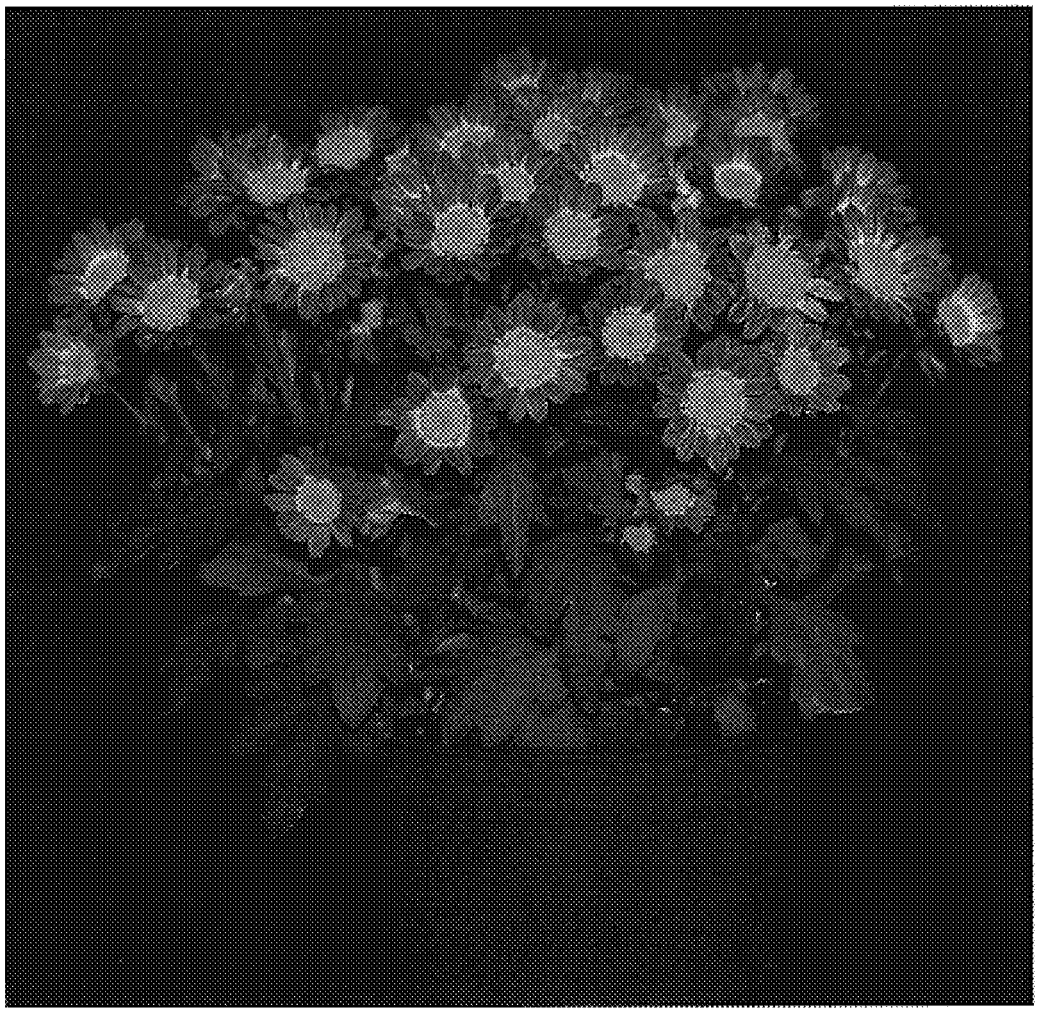

* * * * *